United States Patent [19]

Sherif

[11] 4,411,876
[45] Oct. 25, 1983

[54] PROCESS FOR THE MANUFACTURE OF TRIMAGNESIUM PHOSPHATE OCTAHYDRATE OF HIGH PURITY

[75] Inventor: Fawzy G. Sherif, Stony Point, N.Y.

[73] Assignee: Stauffer Chemical Company, Westport, Conn.

[21] Appl. No.: 454,395

[22] Filed: Dec. 30, 1982

[51] Int. Cl.$^3$ ............................................. C01B 25/26
[52] U.S. Cl. ...................................................... 423/311
[58] Field of Search ............................... 423/308, 311

[56] References Cited

U.S. PATENT DOCUMENTS

| | | | |
|---|---|---|---|
| 991,096 | 5/1911 | Schrödter | 423/311 |
| 2,095,994 | 10/1937 | MacIntire | 423/311 |
| 3,194,632 | 7/1965 | Baniel et al. | 423/311 |

FOREIGN PATENT DOCUMENTS

| | | | |
|---|---|---|---|
| 44-4649 | 2/1969 | Japan | 423/311 |
| 636182 | 12/1978 | U.S.S.R. | 423/311 |

OTHER PUBLICATIONS

Bhaunagary et al., "Preparation of Tricalcium Phosphate by Hydrolysis of Dicalcium Phosphate with Calcium Hydroxide", J. Appl. Chem. Biotechnol., (1977), 27, 393–398.
Chemical Abstracts, 81(12), 71959c.
Chemical Abstracts, 78(22) 138447t.

*Primary Examiner*—Edward J. Meros
*Assistant Examiner*—Wayne A. Langel
*Attorney, Agent, or Firm*—Vivienne T. White

[57] ABSTRACT

The invention is the production of crystalline tertiary magnesium phosphate octahydrate having uniform and perfect crystal shape. The process comprises adding a monomagnesium phosphate solution to a magnesium hydroxide slurry at a sufficient temperature and for a sufficient time to form the highly pure crystalline product within a specified pH range.

9 Claims, No Drawings

PROCESS FOR THE MANUFACTURE OF TRIMAGNESIUM PHOSPHATE OCTAHYDRATE OF HIGH PURITY

BACKGROUND OF THE INVENTION

1. Field of the Invention

The invention relates to a process for the production of tertiary magnesium phosphate octahydrate and in particular to a process for the production of highly pure crystalline tertiary magnesium phosphate octahydrate.

2. Related Art

It is known to use tertiary magnesium phosphate (a/k/a tribasic magnesium phosphate or trimagnesium phosphate), or an alkali metal pyrophosphate as a stabilizer for dibasic calcium phosphate.

It is well known that hardness and particle shape make dibasic calcium phosphate suitable for use as a base for dentifrices. The required properties of a base for a toothpaste are that, even when kept in the tube for a long time, it does not harden, remains homogeneous, does not form a coagulated mass, and does not separate into a liquid and solid phase. However, the dihydrate of dibasic calcium phosphate, when used as a base for a toothpaste is so unstable that it often tends to harden, coagulate, causing the toothpaste to separate into a liquid and a solid phase. The water of crystallization of dibasic calcium phosphate is normally thermally unstable and tends to evaporate readily when the compound is allowed to stand in dry air at room temperature, leaving the anhydrous salt behind.

With the advent of the use of monofluorophosphate additives in toothpaste formulations another problem was encountered. It was found that the monofluorophosphate components would react with the dicalcium phosphate whereby the monofluorophosphate component was converted from a water/soluble form to a water insoluble form. Since the beneficial effect of monofluorophosphate additives in toothpaste is understood to be derived principally from the water-soluble form, it has become important to develop toothpaste formulations which permit an effective amount of monofluorophosphate component to remain in the water-soluble state.

The term "monofluorophosphate compatibility" has been used as a term-of-art to describe the tendency of such formulations to permit the monofluorophosphate component to remain in the water soluble state.

The monofluorophosphate compatibility of a particular formulation may be determined by a variety of methods. Preferably, the monofluorophosphate compatibility of a formulation is determined by actually preparing the toothpaste formulation, comprising a fluoride stabilizer, placing it in storage for a predetermined period of time under controlled conditions, and then determining the amount of water-soluble monofluorophosphate which remains in the formulation. Alternatively, a simulated formulation, such as the dicalcium phosphate dihydrate to be tested, glycerine, a known amount of a monofluorophosphate component, such as sodium monofluorophosphate and a stabilizer can be "quick aged" by maintaining it at an elevated temperature for one or more hours, and then determining the amount of water-soluble monofluorophosphate remaining after such conditioning. There are, of course, many other methods for measuring the relative monofluorophosphate compatibility of various samples of dicalcium phosphate dihydrate.

The prior art teaches that dicalcium phosphate dihydrate may be stabilized by adding a small amount of an alkali metal pyrophosphate or tertiary magnesium phosphate to the mother liquor, at a controlled pH, during the preparation of the dicalcium phosphate. Specifically, it is taught that after precipitation of the dicalcium phosphate in the mother liquor, a small amount of alkali metal pyrophosphate or tertiary magnesium phosphate should be added and the entire slurry then heated for a short period of time, while maintaining the pH of the mother liquor above 7.

The alkali metal pyrophosphate or tertiary magnesium phosphate coats the surface of the dicalcium phosphate such that the coating significantly eliminates the reaction of the dicalcium phosphate with the monofluorophosphate thereby resulting in a dicalcium phosphate which remains in the water soluble state.

The effect of tertiary magnesium phosphate as a stabilizer for dibasic calcium phosphate varies greatly with the method used for its production.

Tertiary magnesium phosphate containing 0, 4, 8, and 22 molecules of water of crystallization has so far been reported, but only the octahydrate is used as a stabilizer for dicalcium phosphate. It is also known to use tribasic magnesium phosphate as a fertilizer because of its high $P_2O_5$ content, and as an antacid. It has also been disclosed to use tribasic magnesium phosphate as a water insoluble neutralizing agent in the growing of acid producing bacteria cultures.

The known production methods for the octahydrate include one in which an aqueous solution of magnesium sulfate and dibasic sodium phosphate is made weakly alkaline with sodium bicarbonate and is then allowed to stand. Another method is one in which dibasic magnesium phosphate is boiled for a long time in a large quantity of water.

It has been disclosed to produce $Mg_3(PO_4)_2.8H_2O$ by the dehydration of $Mg_3(PO_4)_2.22H_2O$ or by the hydrolysis of $Mg_2HPO_4.3H_2O$.

It has also been disclosed to produce $Mg_3(PO_4)_2.8H_2O$ by reacting orthophosphoric acid, added dropwise, to magnesium oxide powder or magnesium hydroxide powder with energetic stirring; see Japanese Patent Application No. 39-57557/1964. This order of addition, i.e., the acid to the base, is disclosed to be necessary to produce the trimagnesium but not the dimagnesium phosphate. However, it is common to produce trimagnesium phosphate by this method, which product is contaminated with unreacted $Mg(OH)_2$ or with dimagnesium phosphate. These undesired components lead to caking. They may also alter the functional properties of the trimagnesium phosphate. Furthermore, the addition of the very strong acid to $Mg(OH)_2$ has to occur at a very slow rate, otherwise the pH falls very quickly forming the dimagnesium phosphate. Therefore, this process takes several hours, normally 10-14 hours, to complete.

SUMMARY OF THE INVENTION

A novel process of producing trimagnesium phosphate octahydrate has been discovered which produces $Mg_3(PO_4)_2.8H_2O$ crystals having good crystal shapes. The process of the invention comprises the reaction of monobasic monomagnesium phosphate with magnesium hydroxide at a temperature of from about 35° C. to about 70° C. for a period of hours wherein the pH is maintained at from about 6.7 to about 6.9 during the process and the process pH is preferably 6.8.

DETAILED DESCRIPTION OF THE INVENTION

The invention is a process of producing highly pure trimagnesium phosphate.

Broadly the invention comprises the preparation of a monomagnesium phosphate solution followed by the addition of the monomagnesium phosphate solution to a magnesium hydroxide slurry wherein the temperature of the slurry is maintained at from about 35° to about 70° C. and preferably from about 40° to about 50° C.

The reactions are thought to be as follows: $Mg(OH)_2$ and excess $H_3PO_4$ are mixed together to produce the following:

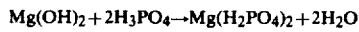

$$Mg(OH)_2 + 2H_3PO_4 \rightarrow Mg(H_2PO_4)_2 + 2H_2O$$

The clear slightly acidic monomagnesium phosphate solution produced has a pH of about 3 to about 3.5. It is then added to a slurry of $Mg(OH)_2$ as shown.

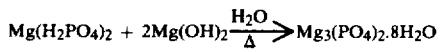

$$Mg(H_2PO_4)_2 + 2Mg(OH)_2 \xrightarrow[\Delta]{H_2O} Mg_3(PO_4)_2 \cdot 8H_2O$$

It is imperative that the order of addition be such that the slightly acidic monomagnesium phosphate solution is added to the magnesium hydroxide slurry otherwise dimagnesium phosphate forms. The highly pure trimagnesium phosphate product formed is highly and uniformly crystalline and has perfect crystal shapes. "Perfect" is defined herein to mean crystallographic data showing no line splitting for the octahydrate product produced in accordance with the invention.

In the practice of the invention, the monomagnesium phosphate solution having a MgO weight concentration of from about 2.0% to about 8.3% and a $P_2O_5$ weight concentration of from about 8% to about 33.1 is produced by mixing a $Mg(OH)_2$ slurry with phosphoric acid solution in water to give a mole ratio of 1 Mg to from about 2 to about 2.4 P. and a pH of from about 3 to about 3.5. Higher concentrations will result in exceeding solubility limits, i.e. precipitation, and lower concentrations are possible but will require longer reaction time per unit production. Ratios of Mg/P as disclosed are necessary to form monomagnesium phosphate $Mg(H_2PO)_2$ as described by the $MgO/P_2O_5/H_2O$ phase diagram appearing in Van Wazer, *Phosphorus and its Compounds*, Vol. 1, p. 539. (Interscience Publishers, Inc., 1958).

The monomagnesium phosphate is then added to a magnesium hydroxide slurry having a MgO weight concentration of from about 8% to about 9% and preferably 8.2% to about 8.7%. Higher concentrations of MgO makes the neutralization reaction sluggish and lower concentrations are possible but will require longer periods of time per unit production. A pH of not lower than 6.7 is desirable during the process with a pH of not less than 6.8 being preferred.

The slurry is maintained at a temperature of from about 35° C. to about 70° C. and preferably from about 40° C. to about 50° C. during the reaction with the monomagnesium phosphate solution.

The addition rate can vary depending upon the amounts of reactants being utilized. Too fast an addition rate will cause the pH to fall below 6.7 and too slow an addition rate will not be economically practical.

A terminal pH of from about 6.7 to about 6.9 for the reaction slurry is generally acceptable with a pH of 6.8 being particularly desirable. At lower a pH of 4 or 6, for example, dimagnesium phosphate is formed instead of trimagnesium phosphate. At higher a pH free untreated $Mg(OH)_2$ remains in the product.

The monomagnesium phosphate solution is generally added to the slurry over a period of time sufficient to complete the reaction and produce the pure trimagnesium phosphate octahydrate product. A total reaction time of from 5 to 7 hours is generally required. After the reaction is completed, the white solid product is filtered from the mother liquor.

In practicing the invention it is desirable to use a monomagnesium phosphate solution having as high a concentration of Mg and $H_3PO_4$ as possible to reduce the amount of filtrate recycled in the commercial process and therefore reduce cost. At lower concentrations of Mg and $H_3PO_4$, the ratio of the filtered product to the mother liquor will be too small, requiring larger equipment in handling of the filtrate. This is not economical.

In the practice of the invention it was discovered that when the reaction of the monomagnesium phosphate solution and the $Mg(OH)_2$ slurry is conducted at a temperature at or less than about 25° C. a mixture of dimagnesium and trimagnesium phosphate with some unreacted $Mg(OH)_2$ is produced. A temperature of above about 70° C. results in producing a product with very fine particles, rendering its filtration tedious.

The following examples are intended only to be illustrative embodiments of the invention.

EXAMPLE 1

A dilute monomagnesium phosphate solution containing 2.54% MgO and 8.95% $P_2O_5$ was prepared by slowly adding 265.3 grams of 12.5% $Mg(OH)_2$ slurry to 637.8 grams of 17.56% $H_3PO_4$ solution at 25° C. over a period of 15 minutes at a flow rate of 25 ml/min. The clear monomagnesium phosphate solution containing a molar ratio of 1 Mg to 2 P was then added to 529.6 grams $Mg(OH)_2$ slurry containing 8.68% MgO at 50° C. at a rate of 2.5 ml/min. while maintaining the pH at 6.8. The total reaction time was 5.5 hours and the terminal pH was 6.8. The product was filtered and dried at 110° C. for 2 hours. The yield was 97% based on the calculated trimagnesium phosphate octahydrate corresponding to the amount of $Mg(OH)_2$ used.

Optical microscopic analysis of the product showed uniform crystal clusters of about 20 m$\mu$ in size. X-ray difraction analysis gave sharp lines with no splitting, indicating perfect crystal shapes. The XRD (x-ray diffraction) of commercial trimagnesium showed split lines, indicatig imperfect crystal orientations.

EXAMPLE 2

A concentrated monomagnesium phosphate solution having maximum concentration with respect to Mg and $H_3PO_4$ at 25° C. that can exist in equilibrium with the monomagnesium phosphate and dimagnesium phosphate hydrates, as described by the phase diagram of the $MgO-P_2O_5-H_2O$ system was utilized in this process. This saturated solution contained 8.3% MgO and 33.1% $P_2O_5$, corresponding to a mole ratio of 1 Mg to 2.26 P.

The monomagnesium phosphate solution was added to a $Mg(OH)_2$ slurry, having the same Mg content as in Example 1, at 50° C. using a flow rate of 0.5 ml/min. to a terminal pH of 6.8. The reaction time was 7 hours.

The yield was 100% based on the amount of magnesium hydroxide used. The crystalline characteristics obtained by optical miscroscopy and XRD were similar to those of the product obtained in Example 1.

EXAMPLE 3

Example 2 was repeated using the same procedure as in Example 1 with the exception that the temperature was 40° C. The reaction time was 7 hours. The yield was 96.7% based on the amount of magnesium hydroxide used. The product was highly crystalline as in Examples 1 and 2.

COMPARATIVE XRD ANALYSIS

X-ray diffraction data (Copper K alpha radiation) as shown in Table I below were obtained for the trimagnesium phosphate octahydrate product from Examples 1, 2 and 3 and were compared with commercially obtained trimagnesium phosphate octahydrate. The x-ray diffraction pattern of products of Examples 1, 2 and 3 have sharp reflection peaks. The major indentifying peak at dÅ 6.73 was a single sharp reflection. The major identifying peak for 12 commercial samples of trimagnesium phosphate octahydrate taken over a 1 year period of production showed the major reflection as a doublet which suggests a distorted crystal shape. The reported diffraction obtained from ASTM files is shown in Table I for comparison:

TABLE I

| X-ray Diffraction, Major 100% Identifying Interplanar Spacing | |
|---|---|
| Product | dÅ |
| Example 1 | 6.73 singlet |
| Example 2 | 6.73 singlet |
| Example 3 | 6.73 singlet |
| Commercially obtained | 6.95 doublet |
| Reported ASTM Card No. 16-330 for $Mg_3(PO_4)_2.8H_2O$ | 6.96 |

COMPARATIVE EXAMPLES 4 AND 5

The process as disclosed in Examples 1 and 2 using dilute and concentrated monomagnesium phosphate solutions respectively were repeated at a reaction temperature of 25° C. in Examples 4 and 5.

The results obtained are shown in Table II.

TABLE II

| Comp. Ex. | Concentration of Monomagnesium Solution | | Terminal pH of $Mg(OH)_2$ | XRD-dÅ Major Line | XRD Interpretation of Products |
|---|---|---|---|---|---|
| | % MgO | % $P_2O_5$ | | | |
| 4 | 2.54 | 8.95 | 6.95 | 7.25 Broad | Tri- and di-magnesium phosphate and $Mg(OH)_2$ |
| 5 | 8.3 | 33.3 | 7 | 7.13, 7.31 Doublet | Tri- and di-magnesium phosphate |

These two examples show the critical effect of temperature on the reaction product. In both Examples made at 25° C., the product was composed of microscopically mixed shape or non-uniform crystals. The XRD main trimagnesium phosphate reflection lines were either broad as in Example 4 or split as in Example 5. In both cases, they were shifted from the dÅ 6.73 of the pure crystals according to this invention. Furthermore, in addition to the trimagnesium phosphate octahydrate, the XRD lines indicate the presence of dimagnesium phosphate trihydrate and traces of $Mg(OH)_2$.

FLUORIDE COMPATABILITY

The fluoride compatibility data shown in Table III below were obtained for Examples 1, 2 and 3 and for Comparative Examples 4 and 5.

A portion of dicalcium phosphate dihydrate was blended with 2% trimagnesium phosphate, by weight of dicalcium phosphate dihydrate, and used to prepare a standard toothpaste formulation which also included sodium monofluorophosphate in an amount equivalent to 1000 ppm. fluride ion.

The toothpaste formulation was then aged for three weeks at 49° C., after which the amount of water soluble monofluorophosphate remaining was determined. The results shown indicate how much of the fluoride ions remains available.

TABLE III

| Sample | Compatability Ppm F- |
|---|---|
| Example 1 | 680 |
| Example 2 | 670 |
| Example 3 | 660 |
| Comparative Example 4 | 600 |
| Comparative Example 5 | 660 |
| Commercially obtained | 585 |

These results show that the trimagnesium phosphate octahydrate prepared by this invention is as good as if not better than the other stabilizers of dicalcium phosphate dentifrice.

What is claimed is:

1. A process for producing trimagnesium phosphate octahydrate having perfect crystal shapes, comprising adding a monobasic monomagnesium phosphate solution to a magnesium hydroxide slurry at a temperature of from about 35° C. to about 70° C. while maintaining the pH at from about 6.7 to about 6.9.

2. The process as claimed in claim 1 wherein the monomagnesium phosphate solution has a pH of from about 3 to about 3.5.

3. The process as claimed in claim 1 wherein the monomagnesium phosphate solution has a MgO concentration of from about 2.0% to about 8.3%.

4. The process as claimed in claim 1 wherein the monomagnesium phosphate solution has a $P_2O_5$ concentration of from about 8% to about 33.1%.

5. The process as claimed in claim 1 wherein the magnesium hydroxide slurry has a MgO concentration of from about 8% to about 9%.

6. The process as claimed in claim 1 wherein the pH does not fall below 6.8 during the process.

7. The process as claimed in claim 1 wherein the terminal pH is 6.8.

8. The process as claimed in claim 1 wherein the process temperature is from about 40° C. to about 50° C.

9. The process as claimed in claim 1 wherein the monomagnesium phosphate solution has a mole ratio of 1 Mg to from about 2 to about 2.4 P.

* * * * *